United States Patent [19]

Heywang et al.

[11] Patent Number: 4,767,444
[45] Date of Patent: Aug. 30, 1988

[54] HERBICIDAL AND MICROBIOCIDAL 2-TRIFLUOROMETHYL-BENZIMIDAZOLES

[75] Inventors: Gerhard Heywang, Bergisch Gladbach; Bernd Baasner; Albrecht Marhold, both of Leverkusen; Ernst Kysela, Bergisch Gladbach; Michael Schwamborn, Cologne; Gerd Hänssler, Leverkusen; Wilfried Paulus, Krefeld; Hans-Joachim Santel, Leverkusen; Robert R. Schmidt, Bergisch Gladbach; Hans-Georg Schmitt, Krefeld, all of Fed. Rep. of Germany

[73] Assignee: Bayer Aktiengesellschaft, Leverkusen, Fed. Rep. of Germany

[21] Appl. No.: 58,062

[22] Filed: Jun. 4, 1987

[30] Foreign Application Priority Data

Jun. 25, 1986 [DE] Fed. Rep. of Germany ....... 3621301

[51] Int. Cl.$^4$ .................. A01N 43/52; C07D 491/05; C07D 235/10
[52] U.S. Cl. .......................................... 71/92; 71/90; 514/394; 548/326; 548/332
[58] Field of Search ................ 548/332, 326; 514/394; 71/90, 92

[56] References Cited

U.S. PATENT DOCUMENTS 3,623,882 11/1971 Gotze et al. .................... 548/326 X

FOREIGN PATENT DOCUMENTS 1642334 4/1971 Fed. Rep. of Germany ...... 548/332
2150219 3/1973 Fed. Rep. of Germany ...... 548/306

OTHER PUBLICATIONS

Adamson, G., et al., *Pestic Sci.* 15, 31 (1984).
Mandel, L., et al., *J. Med. Chemistry*, 1970, vol. 13, No. 6, pp. 1043–1047.
Büchel, K., *Z. Naturforsch*, 256, pp. 934–944 and pp. 945–953.

*Primary Examiner*—Richard A. Schwartz
*Attorney, Agent, or Firm*—Sprung Horn Kramer & Woods

[57] ABSTRACT

The present invention relates to new 2-trifluoromethyl-benzimidazoles of the general formula (I)

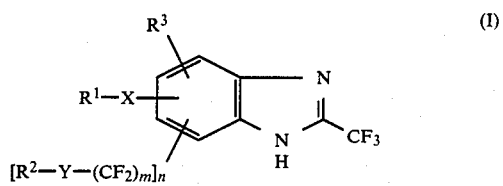

in which
$R^1$ represents halogenoalkyl,
$R^2$ represents optionally substituted alkyl or
$R^1$ and $R^2$ together represent optionally substituted alkylene,
$R^3$ represents hydrogen or alkyl,
X and Y independently of one another represent oxygen and sulphur,
m represents 0 or 1 and
n represents 0 or 1, a process for their preparation and their use as herbicides and microbicides.

12 Claims, No Drawings

HERBICIDAL AND MICROBIOCIDAL 2-TRIFLUOROMETHYL-BENZIMIDAZOLES

The present invention relates to new 2-trifluoromethyl-benzimidazoles, a process for their preparation and their use as herbicides and microbicides.

It is already known that certain 2-trifluoromethylbenzimidazoles have herbicidal, microbicidal, fungicidal and, in some cases, also insecticidal properties [see, for example, DE-OS (German Published Specification) No. 1,642,334, DE-AS (German Published Specification) No. 2,150,219, Pestic Sci. 15, 31 (1984), J. med. Chem. 13, 1043 (1970), Z. Naturforsch. 256, 934 and 945 (1970)]. However, in certain areas of indication the action of these compounds is not always satisfactory under certain conditions, for example at low application rates and concentrations.

New 2-trifluoromethyl-benzimidazoles of the general formula (I)

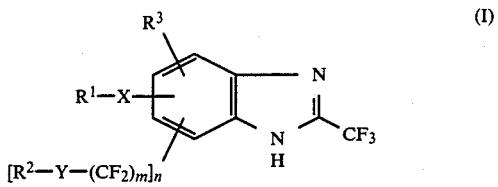

in which
R$^1$ represents halogenoalkyl,
R$^2$ represents optionally substituted alkyl or
R$^1$ and R$^2$ together represent optionally substituted alkylene,
R$^3$ represents hydrogen or alkyl,
X and Y independently of one another represent oxygen and sulphur,
m represents 0 or 1 and
n represents 0 or 1,
have now been found.

It has also been found that the new 2-trifluoromethyl-benzimidazoles of the formula (I)

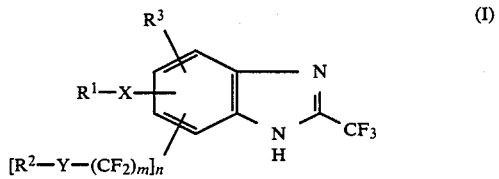

in which
R$^1$ represents halogenoalkyl,
R$^2$ represents optionally substituted alkyl or
R$^1$ and R$^2$ together represent optionally substituted alkylene,
R$^3$ represents hydrogen or alkyl,
X and Y independently of one another represent oxygen and sulphur,
m represents 0 or 1 and
n represents 0 or 1,
are obtained if o-phenylenediamines of the formula (II)

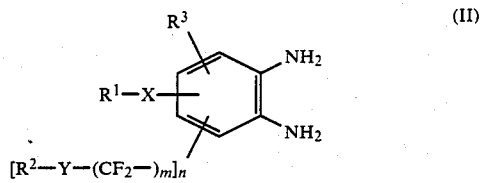

in which
R$^1$, R$^2$, R$^3$, X, Y, m and n have the meaning given above,
are reacted with trifluoroacetic acid, if appropriate in the presence of concentrated hydrochloric acid and if appropriate in the presence of a diluent.

Finally, it has been found that the new 2-trifluoromethyl-benzimidazoles of the formula (I) have herbicidal, in particular selective herbicidal, microbicidal and fungicidal properties.

Surprisingly, the 2-trifluoromethyl-benzimidazoles according to the invention, of the formula (I), exhibit not only better herbicidal activity against weeds but also excellent toleration by crop plants and furthermore exhibit better microbicidal and fungicidal activity than the benzimidazoles which are known from the prior art and have the same type of action.

Within the scope of the above definitions of substituents, alkyl preferably represents a straight-chain or branched saturated hydrocarbon having 1 to 6 carbon atoms, particularly preferably having 1 to 5 carbon atoms, such as, for example, methyl, ethyl, n- and i-propyl, n-, i-, s- and t-butyl and n- and i-pentyl.

Halogenoalkyl preferably represents a straight-chain or branched saturated hydrocarbon having 1 to 6 carbon atoms and 1 to 13 identical or different halogen atoms, particularly preferably having 1 to 4 carbon atoms and 1 to 9 identical or different halogen atoms (such as fluorine, chlorine or bromine), in particular having 1 or 2 carbon atoms and 1 to 5 identical or different halogen atoms (such as fluorine and chlorine), such as, for example, trifluoromethyl, trichloromethyl, trifluorochloromethyl and trifluoroethyl.

Alkylene preferably represents a straight-chain or branched saturated hydrocarbon having 1 to 4 carbon atoms, particularly preferably having 1 or 2 carbon atoms, such as, for example, methylene and ethylene.

Halogen represents fluorine, chlorine, bromine and iodine, preferably fluorine, chlorine and bromine and in particular fluorine and chlorine.

Formula (I) gives a general definition of the 2-trifluoromethyl-benzimidazoles according to the invention. Preferred compounds of the formula (I) are those in which
R$^1$ represents halogenoalkyl having 1 to 6 carbon atoms and 1 to 13 identical or different halogen atoms,
R$^2$ represents alkyl having 1 to 6 carbon atoms which is optionally monosubstituted or polysubstituted by identical or different substituents from amongst fluorine, chlorine and bromine, or
R$^1$ and R$^2$ together represent alkylene having 1 to 4 carbon atoms which is optionally monosubstituted or polysubstituted by identical or different substituents from amongst fluorine, chlorine and bromine,
R$^3$ represents hydrogen or alkyl having 1 to 6 carbon atoms, X and Y independently of one another represent oxygen and sulphur, m represents 0 or 1 and n represents 0 or 1.

Particularly preferred 2-trifluoromethylbenzimidazoles of the formula (I) are those in which R¹ represents halogenoalkyl having 1 to 4 carbon atoms and 1 to 9 identical or different fluorine, chlorine or bromine atoms, R² represents alkyl having 1 to 4 carbon atoms which is optionally monosubstituted to nonasubstituted by identical or different substituents from amongst fluorine and chlorine, or R¹ and R² together represent alkylene having 1 to 4 carbon atoms which is optionally monosubstituted to pentasubstituted by identical or different substituents from amongst fluorine and chlorine, R³ represents hydrogen or alkyl having 1 to 4 carbon atoms, X and Y independently of one another represent oxygen and sulphur, m represents 0 or 1 and n represents 0 or 1.

Very particularly preferred compounds of the formula (I) are those in which

R¹ represents fluoromethyl, difluoromethyl, trifluoromethyl, chloromethyl, dichloromethyl, trichloromethyl, chlorodifluoromethyl, dichlorofluoromethyl, 1,1,2,2-tetrafluoroethyl, 2-chloro-1,1,2-trifluoroethyl, 2,2,2-trifluoroethyl, 2,2-dichloro-1,1,2-trifluoroethyl, 2-chloro-1,1,2,2-tetrafluoroethyl, 2-chloro-2,2-difluoroethyl, 2,2-dichloro-2-fluoroethyl, 2,2,2-trichloroethyl or 1,1,2,3,3-hexafluoropropyl, R² stands fluoromethyl, difluoromethyl, trifluoromethyl, chloromethyl, dichloromethyl, trichloromethyl, chlorodifluoromethyl, dichlorofluoromethyl, 1,1,2,2-tetrafluoroethyl, 2-chloro-1,1,2-trifluoroethyl, 2,2,2-trifluoroethyl, 2,2-dichloro-1,1,2-trifluoroethyl, 2-chloro-1,1,2,2-tetrafluoroethyl, 2-chloro-2,2-difluoroethyl, 2,2-dichloro-2-fluoroethyl, 2,2,2-trichloroethyl or 1,1,2,3,3-hexafluoropropyl, or R¹ and R² together represent difluoromethylene, chlorofluoromethylene, α,β-difluoroethylene, α,α-difluoroethylene, trifluoroethylene, tetrafluoroethylene, chlorotrifluoroethylene, chlorodifluoroethylene, chlorofluoroethylene or dichlorofluoroethylene, R³ represents hydrogen, methyl, ethyl, propyl and isopropyl and X, Y, m and n have the meaning given above.

The following new 2-trifluoromethyl-benzimidazoles of the formula (I) may be mentioned specifically by way of example:

4-trifluoromethoxy-2-trifluoromethyl-benzimidazole
7-trifluoromethoxy-2-trifluoromethyl-benzimidazole
5-trifluoromethoxy-2-trifluoromethyl-benzmidazole
6-trifluoromethoxy-2-trifluoromethyl-benzimidazole
4-trifluoromeththio-2-trifluoromethyl-benzimidazole
5-trifluoromeththio-2-trifluoromethyl-benzimidazole
4-[2,2,2-trifluoroethoxy]-2-trifluoromethyl-benzimidazole
5-[2,2,2-trifluoroethoxy]-2-trifluoromethyl-benzimidazole
4-[1,1,2,2-tetrafluoroethoxy]-2-trifluoromethyl-benzimidazole
4-[2-chloro-1,1,2-trifluoroethoxy]-2-trifluoromethyl-benzimidazole
5-[1,1,2,2-tetrafluoroethoxy]-2-trifluoromethyl-benzimidazole
5-[2-chloro-1,1,2-trifluoroethoxy]-2-trifluoromethyl-benzimidazole
4,5-bistrifluoromethoxy-2-trifluoromethyl-benzimidazole
5,6-bistrifluoromethoxy-2-trifluoromethyl-benzimidazole
4,6-bistrifluoromethoxy-2-trifluoromethyl-benzimidazole
5-methoxy-6-trifluoromethoxy-2-trifluoromethyl-benzimidazole
5,6-difluoromethylene-dioxy-2-trifluoromethyl-benzimidazole
5,6-trifluoroethylene-dioxy-2-trifluoromethyl-benzimidazole
5,6-tetrafluoroethylene-dioxy-2-trifluoromethyl-benzimidazole
5,6-chlorotrifluoroethylene-dioxy-2-trifluoromethyl-benzimidazole
6-[2-chloro-1,1,2-trifluoroethoxy]-5-methyl-2-trifluoromethyl-benzimidazole
5-[2-chloro-1,1,2-trifluoromethoxy]-6-methyl-2-trifluoromethyl-benzimidazole
7,7,9,9-tetrafluoro-6,7,8,9-tetrahydro-2-trifluoromethyl-6,8-dioxabenzo[g]benzimidazole.

If, for example, 2-trifluoromethoxy-5,6-diaminobenzene and trifluoroacetic acid are used as starting materials, the course of the reaction of the process according to the invention can be represented by the following equation:

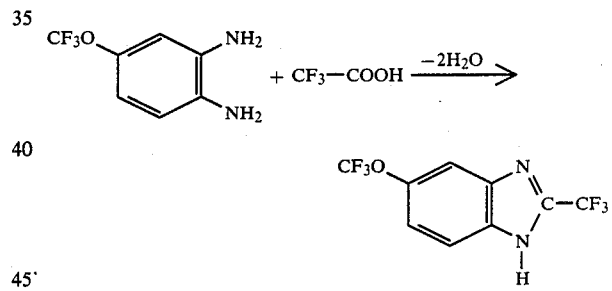

Formula (II) gives a general definition of the o-phenylenediamines required for carrying out the process according to the invention. In this formula, R¹, R², R³, X, Y, m and n have the meaning which has already been mentioned for these symbols in connection with the description of the substances according to the invention, of the formula (I).

Some of the starting materials of the formula (II) are known (see, for example, EP-A-127,763). Some of the o-phenylenediamines of the formula (II) form the subject of German Patent Application DE No. P 3,605,977 of Feb. 25, 1986, corresponding to U.S. Application Ser. No. 12,523, filed Feb. 9, 87, and some of them form the subject of German Patent application No. 3,621,265, filed June 25, 86.

The new and the known compounds of the general formula (II) can be prepared (see, for example, L. M. Yagupolskij et al., Zh. Obsh. Khim 33, 3051-5 (1963); Houben-Weyl, Volume X/1, page 559 (1971) and Volume XI/1, pages 472-3 (1957) and preparation examples), by, for example, first acylating the amino group of compounds of the formula (III)

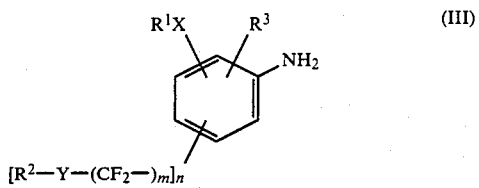

in which

R1, R2, R3, X, Y, m and n have the meaning given above, and introducing a nitro group in the 2-position with respect to the acylated amino group with a nitrating agent, such as, for example, nitrating acid, if appropriate in the presence of a diluent, such as, for example, glacial acetic acid, and, if appropriate, in the presence of a catalyst, such as, for example, acetic anhydride, at temperatures between −20° and +50° C., hydrogenating the nitro group to the amino group in the presence of a catalyst, such as, for example, Raney nickel, and in the presence of a diluent, such as, for example, methanol, under hydrogen pressures of 10 to 100 bar and at temperatures between +20° and +80° C., and then eliminating the acyl group again in a customary manner, for example by hydrolysis with aqueous or alcoholic base.

The compounds of the formula (III) are known and can be prepared by known processes in an analogous manner (see, for example, European Patent 11,179).

The trifluoroacetic acid furthermore required for carrying out the process according to the invention is a known compound of organic chemistry.

Suitable diluents for carrying out the process according to the invention are inert organic solvents, for example toluene, chlorobenzene and dichlorobenzene. Toluene is preferably used.

The reaction can also be carried out in concentrated aqueous hydrochloric acid according to M. A. Phillips, J. Chem. Soc. 1928, 2393.

In carrying out the process according to the invention, the reaction temperatures can be varied in a relatively wide range. In generaly, the reaction is carried out at temperatures between 20° C. and 220° C., preferably between 20° C. and 160° C. or at the boiling point of the lowest boiling component in each case from amongst the components present in the reaction mixture.

The process according to the invention is generally carried out under atmospheric pressure. However, elevated or reduced pressure can also be employed.

To carry out the process according to the invention, in general 1 to 20 mols, preferably 1 to 10 mols, particularly preferably 1.1 to 5 mols, of trifluoroacetic acid are employed per mol of o-phenylenediamine of the formula (II).

The o-phenylenediamines of the formula (II) can be used in the process according to the invention also in the form of their salts, formed from (II) and a suitable organic acid, such as, for example, acetic acid, or as hydrochlorides. The acylated diamines too can be used for carrying out the process according to the invention.

Working up, isolation and characterization of the 2-trifluoromethyl-benzimidazoles of the formula (I) are carried out by generally customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The substances according to the invention, of the formula (I) exhibit not only particularly good general herbicidal activity but also clearly improved selectivity with respect to crop plants in important cultures and can be used as selective weedkillers, in particular against dicotyledon weeds, in dicotyledon cultures, such as, for example, cotton, and also in monocotyledon cultures, in particular cereals, such as, for example, wheat, by the pre-emergence and post-emergence method. Particularly in the post-emergence method, the compounds according to the invention, of the formula (I), are also suitable for combating monocotyledon weeds.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersion agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesive such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

If used as herbicide or fungicide, the formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beets and 4-amino-6-(1,1-dimethylethyl)-3-methylthio-1,2,4-triazin-5(4H)-one for combating weeds in soybeans.

Mixtures with chloroacetic acid N-(methoxymethyl)-2,6-diethylanilide, 2-ethyl-6-methyl-N-(1-methyl-2-methoxyethyl)-chloroacetanilide, N-methyl-2-(1,3-benzothiazol-2-yloxy)-acetanilide, S-(2,3,3-trichloroallyl) N,N-diisopropylthiolcarbamate, S-ethyl N,N-di-n-propyl-thiocarbamate, exo-1-methyl-4-(1-methylethyl)-2-(2-methylphenylmethoxy)-7-oxabicyclo[2,2,1]heptane, 1-methyl-3-phenyl-5-[3-trifluoromethyl-phenyl]-4(1H)-pyridinone, methyl 2-[4,5-dihydro-4-methyl-4-(1-methylethyl)-5-oxo-1H-imidazol-2-yl]-4(5)-methylbenzoate, 2-[1-(ethoxamino)butylidene]-5-(2-ethylthiopropyl)-1,3-cyclohexanedione, 3-isopropyl-2,1,3-benzothiadiazin-4-one 2,2-dioxide, 6-chloro-3-phenyl-pyridazin-4-yl S-octyl thiocarbonate, N-benzothiazolyl-N-methyl-N'-(3-chloro-4-methylphenyl)-urea, 2-chloro-N-{[(4-methoxy-6-methyl-1,3,5-triazin-2-yl)amino]-carbonyl}-benzenesulphonamide, N,N-dimethyl-N'-(4-isopropylphenyl)-urea, N,N-dimethyl-N'-(3-trifluoromethyl-phenyl)-urea, 4-ethylamino-2-t-butylamino-6-methylthio-s-triazine, 2-chloro-4,6-bis(ethylamino)-1,3,5-triazine, 2-chloro-4-ethylamino-6-isopropylamino-1,3,5-triazine, 2-chloro-4-ethylamino-6-(3-cyanopropylamino)-1,3,5-triazine, 4-amino-6-tert.-butyl-3-methylthio-4,5-dihydro-1,2,4-triazin-5-one, trimethylsilylmethyl 2-[4,$\beta$,5-dichloropyrid-2-yloxy)-phenoxyl]-propionate, 2-{4-[(3-chloro-5-trifluoromethyl-2-pyridyl)-oxy]-phenoxy}-propanoic acid, methyl 2-[4-(2,4-dichlorophenoxy)-phenoxy]-propionate, 2,4-dichlorophenoxyacetic acid, 2,4-dichlorophenoxy-propionic acid, (2-methyl-4-chlorophenoxy)-acetic acid, (4-chloro-2-methyl-phenoxy)-propionic acid, methyl 5-(2,4-dichlorophenoxy)-2-nitrobenzoate, 3,5-diiodo-4-hydroxybenzonitrile, 3,5-dibromo-4-hydroxybenzonitrile and N-(1-ethoxypropyl)-3,4-dimethyl-2,6-dinitroaniline are also suitable. Surprisingly, some mixtures show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering. It is also possible to apply the active compounds by the ultralow volume method or to inject the active compound preparation or the active compound itself into the soil. The seed of the plants can also be treated.

The active compounds according to the invention can be applied either before or after emergence of the plants.

They can also be incorporated into the soil before sowing.

For use as a herbicide, the amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The 2-trifluoromethyl-benzimidazoles of the formula (I) also have a powerful microbicidal action and can be used for combating undesired microorganisms. The active compounds are suitable for use as plant protection agents, in particular as fungicides, or can be used in material protection for protecting industrial materials.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae,* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

For use as a fungicide in the treatment of parts of plants, the active compound concentrations in the use forms can be varied within a substantial range. They are in general between 1 and 0.0001% by weight, preferably between 0.5 and 0.001%.

In the treatment of seed, amounts of active compound of from 0.001 to 50 g per kilogram of seed, preferably 0.01 to 10 g, are generally required.

In the treatment of the soil, active compound concentrations of 0.00001 to 0.1% by weight, preferably 0.0001 to 0.02%, are required at the place of action.

The active compounds according to the invention, of the formula (I), also have good activity in combating soil insects and nematodes.

According to the invention, industrial materials are non-living materials which have been prepared for use in industry. For example, industrial materials which are to be protected by the active compounds according to the invention from microbial modification or destruction can be adhesives, glues, paper and cardboard, textiles, leather, wood, coating agents and plastic articles, cooling lubricants and other materials which can be attacked or destroyed by microorganisms. Parts of production plants, for example cooling water circulations, which can be adversely affected by multiplication of microorganisms may also be mentioned within the scope of the materials to be protected. Industrial materials which may be preferably mentioned within the scope of the present invention are adhesives, glues, papers and cardboards, leather, wood, coating agents, cooling lubricants and cooling circulations.

Bacteria, fungi, yeasts, algae and slime organisms may be mentioned as examples of microorganisms which can cause degradation or modification of the industrial materials. The active compounds according to the invention preferably act against fungi, in particular moulds, wood-discolouring and wood-destroying fungi (Basidiomycetes), and against bacteria, slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeroginosa,*
Staphylococcus, such as *Staphylococcus aureus.*

An active compound according to the invention can be converted to the customary formulations, such as solutions, emulsions, suspensions, powders, pastes and granules, depending on the field of use.

These can be prepared in a manner known per se, for example by mixing the active compounds with an extender which consists of a liquid solvent and/or solid carriers, if appropriate with the use of surface-active agents, such as emulsifiers and/or dispersants, it being possible, if required, to use organic solvents, such as alcohols, as auxiliaries in the case of the use of water.

Liquid solvents of the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

Microbicidal agents contain the active compounds in general in an amount of 1 to 95%, preferably 10 to 75%.

The use concentrations of the active compounds according to the invention depend on the type and occurrence of the microorganisms to be combated and on the composition of the material to be protected. The optimum amount for use can be determined by test series. In general, the use concentrations are in the range from 0.001 to 5% by weight, preferably from 0.05 to 1.0% by weight, relative to the material to be protected.

The active compounds according to the invention can also be present as a mixture with other known active compounds. The following active compounds may be mentioned as examples: benzyl alcohol mono(poly)-hemiformal and other formaldehyde-donating compounds, benzimidazolyl methylcarbamates, tetramethylthiuram disulphide, zinc salts of dialkyldithiocarbamates, 2,4,5,6-tetrachloroisophthalonitrile, .thiazolylbenzimidazole, mercaptobenzothiazole, 2-thiocyanatomethylthiobenzothiazole, organotin compounds, methylenebisthiocyanate, and phenol derivatives, such as 2-phenylphenol, (2,2'-dihydroxy-5,5'-dichloro)-diphenylmethane and 3-methyl-4-chlorophenol.

The preparation and the use of the active compounds according to the invention are evident from the examples which follow.

PREPARATION EXAMPLES

EXAMPLE 1

2-Trifluoromethyl-5,5,6,6-tetrafluoroethylenedioxybenzimidazole

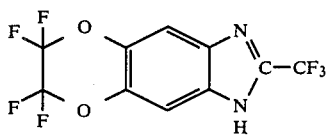

45 g (0.39 mol) of trifluoroacetic acid are added dropwise to 23.8 g (0.1 mol) of 2,2,3,3,-tetrafluoro-6,7-diamino-benzo-1,4-dioxene in the course of about 20 minutes. The temperature increases from 20° C. to about 60° C., and no cooling is carried out. Thereafter, the mixture is heated to 130° C. (bath temperature) in the course of about 30 minutes and stirred for a further 2 hours at this temperature. After cooling, the mixture is rendered alkaline by the dropwise addition of 120 ml of 10% strength sodium hydroxide solution, and the precipitated solid is filtered off under suction, rinsed with water and dried.

Yield: 28.1 g (88.8% of theory) Melting point: 235°–237° C.

The compounds of the formula (I) which are listed in Table 1 below are obtained in an analogous manner:

TABLE 1

| Example No. | Compound | M.p. (°C.) |
|---|---|---|
| 2 | 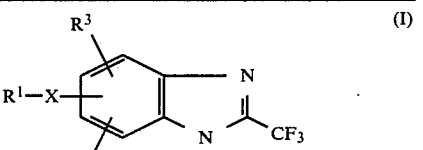 | 203–205 |
| 3 | | 257–259 |
| 4 | | 157–158 |
| 5 | | 167–168 |
| 6 | | 155–156 |
| 7 | | 175–176 |
| 8 | | 188–189 |
| 9 | | 158–160 |
| 10 | | 235–237 |

Preparation of the starting materials

EXAMPLE II-1

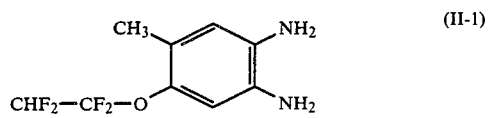

(a) Acylation 114 g (0.51 mol) of 4-methyl-5-(1,1,2,2-tetrafluoroethoxyaniline) are added dropwise to a solution, at 50°

C., of 60 g of acetic anhydride, 20 g of a acetic acid and 2 ml of pyridine. The mixture is stirred for a further two hours at 50° C. and then worked up by adding water. 132 g of 4-methyl-5-(1,1,2,2-tetrafluoroethoxy)acetanilide (M.p.: 124° C.) are obtained.

(b) Nitration 132 g (0.5 mol) of 4-methyl-5-(1,1,2,2-tetrafluoroethoxy)-acetanilide are nitrated with the addition of 165 g of nitrating acid (33% by weight of $HNO_3$ and 67% by weight of $H_2SO_4$) and 25 g of water at 0° to 5° C. After working up by adding water, 110 g of crude 2-nitro-4-methyl-5-(1,1,2,2-tetrafluoroethoxy)-acetanilide are obtained.

(c) Hydrogenation

The nitrated product is hydrogenated in 250 ml of methanol with the addition of 10 g of Raney nickel at 50° C. and 30–50 bar hydrogen pressure. After the Raney nickel and the methanol have been separated off, 90 g of crude 2-amino-4-methyl-5-(1,1,2,2-tetrafluoroethoxy)-acetanilide are obtained.

(d) Hydrolysis 350 ml of methanol and 100 g of 50% strength by weight aqueous sodium hydroxide solution are added to the hydrogenated product, and the mixture is stirred for 5 hours at 45° C. and for a further 7 hours at 25° C. After working up by adding water, 68 g of 2-amino-4-methyl-5-(1,1,2,2-tetrafluoroethoxy)-aniline of boiling point 105°–107° C./0.04 l mbar and melting point 99°–103° C. are obtained.

The o-phenylenediamines of the formula (II) which are listed in Table 2 below are obtained in an analogous manner:

TABLE 2

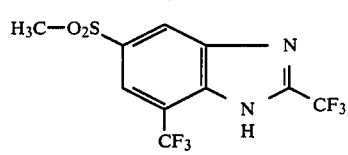

(A)

(disclosed in DE-OS (German Published Specification) No. 1,642,334, Example 6)

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, in addition to very good toleration by

| Example No. | $[R^2-Y-(CF_2-)_m]_n$ | $R^1-X$ | $R^3$ | Boiling point (°C./mbar) | Melting point (°C.) |
|---|---|---|---|---|---|
| II-2 | 4-OCF$_3$ | 5-OCF$_3$ | H | 121/12 | — |
| II-3 | 4-OCF$_3$ | 5-OCH$_3$ | H | 130/12 | — |
| II-4 | — | 3-OCF$_3$ | H | 102/6 | 45–47 |
| II-5 | — | 5-OCF$_2$CF$_2$H | 4-CH$_3$ | 120–5/0.01 | |

EXAMPLE II-6

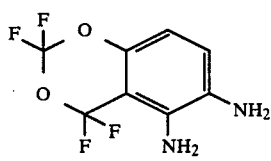

Melting point: 50°–52° C.

USE EXAMPLES

In the herbicidal tests below, the following compound is used as a comparative substance:

crop plants such as cotton and wheat, substantially better herbicidal activity against weeds, such as, for example, Datura, Galium, Solanum, Viola, Cynodon and Poa, compared with the comparative compound (A), is shown by, for example, the compound according to preparation Example 7.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, substantially better herbicidal activity against weeds, such as, for example, Amaranthus, Datura, Ipomoea, Solanum, Panicum and Setaria, compared with the comparative substance (A), is shown by, for example, the compounds according to preparation Example 1 and 7.

EXAMPLE C

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a substantially superior activity compared with the prior art is shown by, for example, the compounds according to the following preparation examples: 1, 2 and 8.

EXAMPLE D

In order to demonstrate the activity against fungi, the minimum inhibitory concentrations (MIC) of active compounds according to the invention are determined:

Active compounds according to the invention are added, in concentrations of 0.1 mg/l to 5,000 mg/l, to an agar prepared from beer wort and peptone. After the agar has solidified, it is contaminated with pure cultures of the test organisms listed in the table. After storage for 2 weeks at 28° C. and 60 to 70% relative atmospheric humidity, the MIC is determined. MIC is the lowest concentration of active compound at which the microbe species used shows no growth at all. Good actions are shown, for example, by the compounds according to preparation Examples 5 and 7 against the test organisms:

*Alternaria tenuis*
*Aspergillus niger*
*Aureobasidium pullulans*
*Chaetomium globosum*
*Cladosporium cladosporioides*
*Lentinus tigrinus*
*Penicillium glaucum*
*Sclerophoma pityophila*
*Trichoderma viride*

EXAMPLE E

Action against bacteria

Active compounds according to the invention are added, in concentrations of 1 to 5,000 ppm, to an agar which contains broth as the nutrient medium. The nutrient medium is then infected with each of the test organisms listed in Table E, and the infected medium is kept for 2 weeks at 28° C. and 60 to 70% relative atmospheric humidity. The MIC is the lowest concentration of active compound at which the microbe species used shows no growth at all. The MIC values are reproduced in Table E.

TABLE E

The MIC values are stated in mg/l for the action of the active compounds stated below on bacteria.

| Test organisms | MIC in mg/l of the active compound | |
|---|---|---|
| | (5) | (7) |
| *Escherichia coli* | 100 | <20 |
| *Staphylococcus aureus* | <20 | <20 |

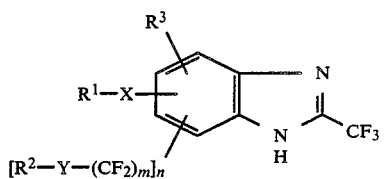

(5)  (7)

It will be understood that the specification and examples are illustrative but not limitative of the present invention and that other embodiments within the spirit and scope of the invention will suggest themselves to those skilled in the art.

We claim:

1. A 2-trifluoromethyl-benzimidazole of the formula in which $R^1$ represents halogenoalkyl having 1 to 6 carbon atoms and 1 to 13 identical or different halogen atoms, $R^2$ represents alkyl having 1 to 6 carbon atoms which is optionally substituted by fluorine, chlorine and/or bromine, or $R^1$ and $R^2$ together represent alkylene having 1 to 4 carbon atoms which is optionally substituted by fluorine, chlorine and/or bromine, and $R^3$ represents hydrogen or alkyl having 1 to 6 carbon atoms x and y independently of one another represent oxygen and sulphur m represents 0 or 1, and n represents 0 or 1.

2. A 2-trifluoromethylbenzimidazole according to claim 1, in which $R^1$ represents halogenoalkyl having 1 to 4 carbon atoms and 1 to 9 identical or different fluorine, chlorine or bromine atoms, R² represents alkyl having 1 to 4 carbon atoms which is optionally monosubstituted to nonasubstituted by fluorine and/or chlorine, or R¹ and R² together represent alkylene having 1 to 4 carbon atoms which is optionally substituted by fluorine and/or chlorine, and R³ represents hydrogen or alkyl having 1 to 4 carbon atoms.

3. A compound according to claim 1, wherein such compound is 2-trifluoromethyl-5,5,6,6-tetrafluoroethylenedioxybenzimidazole

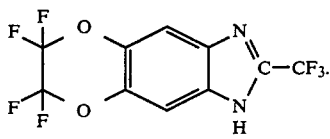

4. A compound according to claim 1, wherein such compound is 2-trifluoromethyl-6-chloro-5,5,6-trifluoroethyledioxybenzimidazole

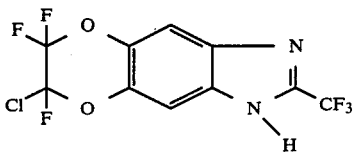

5. A compound according to claim 1, wherein such compound is 2-trifluoromethyl-5-trifluoromethoxy-benzimidazole

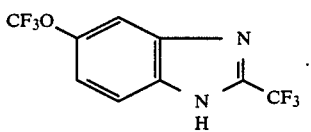

6. A compound according to claim 1, wherein such compound is 2-trifluoromethyl-5-trifluoromethylthiobenzimidazole

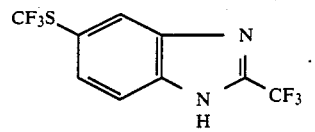

7. A compound according to claim 1, wherein such compound is 2-trifluoromethyl-5-(1,1,2,2-tetrafluoroethoxy)benzimidazole

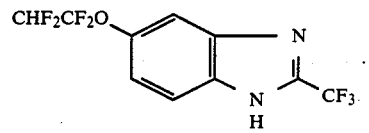

8. A herbicidal or microbicidal composition comprising a herbicidally or microbicidally effective amount of a compound according to claim 1 and a diluent.

9. A method of combating unwanted vegetation which comprises applying to said vegetation or to a locus from which it is desired to exclude such vegetation a herbicidally effective amount of a compound according to claim 1.

10. The method according to claim 9, wherein such compound is
2-trifluoromethyl-5,5,6,6-tetrafluoroethylenedioxybenzimidazole,
2-trifluoromethyl-6-chloro-5,5,6-trifluoroethyledioxybenzimidazole,
2-trifluoromethyl-5-trifluoromethoxy-benzimidazole,
2-trifluoromethyl-5-trifluoromethylthiobenzimidazole, or
2-trifluoromethyl-5-(1,1,2,2-tetrafluoroethoxy)benzimidazole.

11. A method of combating unwanted microbes which comprises applying to such microbes or to a locus from which it is desired to exclude such microbes a microbicidally effective amount of a compound according to claim 1.

12. The method according to claim 11, wherein such compound is
2-trifluoromethyl-5,5,6,6-tetrafluoroethylenedioxybenzimidazole,
2-trifluoromethyl-6-chloro-5,5,6-trifluoroethyledioxybenzimidazole,
2-trifluoromethyl-5-trifluoromethoxy-benzimidazole,
2-trifluoromethyl-5-trifluoromethylthiobenzimidazole, or
2-trifluoromethyl-5-(1,1,2,2-tetrafluoroethoxy)benzimidazole.

* * * * *